United States Patent
Healy et al.

(10) Patent No.: US 7,475,245 B1
(45) Date of Patent: Jan. 6, 2009

(54) SYSTEM AND METHOD FOR PROVIDING SECURE EXCHANGE OF SENSITIVE INFORMATION WITH AN IMPLANTABLE MEDICAL DEVICE

(75) Inventors: Scott J. Healy, Maple Grove, MN (US); Jeffrey A. Von Arx, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 771 days.

(21) Appl. No.: 10/801,150

(22) Filed: Mar. 15, 2004

(51) Int. Cl.
*H04L 9/08* (2006.01)

(52) U.S. Cl. .......................... 713/168; 607/57; 607/59; 607/60

(58) Field of Classification Search .............. 713/168; 607/59
See application file for complete search history.

(56) References Cited

U.S. PATENT DOCUMENTS

| | | | |
|---|---|---|---|
| 5,113,869 A | 5/1992 | Nappholz et al. | |
| 5,720,770 A | 2/1998 | Nappholz et al. | |
| 5,752,976 A | 5/1998 | Duffin et al. | |
| 6,024,699 A | 2/2000 | Surwit et al. | |
| 6,083,248 A | 7/2000 | Thompson | |
| 6,171,256 B1 | 1/2001 | Joo et al. | |
| 6,416,471 B1 | 7/2002 | Kumar et al. | |
| 6,434,429 B1 | 8/2002 | Kraus et al. | |
| 6,442,432 B2 * | 8/2002 | Lee ............................ | 607/59 |
| 6,493,587 B1 * | 12/2002 | Eckmiller et al. ............. | 607/31 |
| 6,827,670 B1 | 12/2004 | Stark et al. | |
| 6,983,381 B2 | 1/2006 | Jerdonek | |
| 7,027,872 B2 * | 4/2006 | Thompson ................... | 607/60 |
| 2001/0023360 A1 * | 9/2001 | Nelson et al. ................ | 607/60 |
| 2001/0027331 A1 | 10/2001 | Thompson | |
| 2001/0039504 A1 | 11/2001 | Linberg et al. | |
| 2002/0016913 A1 | 2/2002 | Wheeler et al. | |
| 2002/0065099 A1 | 5/2002 | Biorndahl | |

FOREIGN PATENT DOCUMENTS

EP  0 756 397  1/1997

OTHER PUBLICATIONS

B. Schneier, "Applied Cryptography, Second Edition," Applied Cryptography. Protocols, Algorithms, and Source Code Inc., John Wiley & Sons, p. 31-42 (1996).
Health Insurance Portability And Accountability Act of 1996, Pub. L. No. 104-191, 110 Stat. 1936 (1996).
W. Diffie, "The First Ten Years Of Public-Key Cryptography," Proceedings of the IEEE, vol. 76, No. 5, pp. 560-577 (May 1988).
E. Hammond, "National Committee On Vital And Health Statistics, Subcommittee On Health Data Needs, Standards And Security," http://www.ncvhs.hhs.gov/970211t3.htm, pp. 1-4 (Feb. 11, 1997).
Security And Electronics Signature Standards, 63 Fed. Reg. 155 (proposed Aug. 12, 1998) (to be codified at 45 C.F.R. pt. 142).

* cited by examiner

*Primary Examiner*—Andrew L Nalven
(74) *Attorney, Agent, or Firm*—Patrick J. S. Inouye; Krista A. Wittman

(57) ABSTRACT

A system and method for providing secure exchange of sensitive information with an implantable medical device is presented. A crypto key uniquely associated with an implantable medical device is defined to encrypt sensitive information during a data exchange session. The crypto key is securely obtained over a secure connection from a secure key repository securely maintaining the crypto key. The sensitive information is encrypted using the crypto key and the sensitive information is stored as encrypted data onto the implantable medical device.

28 Claims, 7 Drawing Sheets

SYSTEM AND METHOD FOR PROVIDING SECURE EXCHANGE OF SENSITIVE INFORMATION WITH AN IMPLANTABLE MEDICAL DEVICE

FIELD OF THE INVENTION

The present invention relates in general to data exchange session authentication and, specifically, to a system and method for providing secure exchange of sensitive information with an implantable medical device.

BACKGROUND OF THE INVENTION

Heart diseases refer to several classes of cardio and cardiovascular disorders and co-morbidities relating to the heart and blood vessels. Heart disease is often treated through a combination of medication and lifestyle modification. In severe cases, a monitoring or therapy delivery device, referred to as an implantable medical device (IM), is surgically implanted to collect cardiac performance data and to deliver therapy to the heart, when needed. IMDs are also used in other areas of medicine to provide neural stimulation, dispense drugs, and perform other monitoring and in situ therapeutic functions, as would be appreciated by one skilled in the art.

Static data can be stored on an IMD for retrieval by health care providers and for use by the IMD. In addition, data collected by the IMD can be downloaded for analysis and, if required, new performance instructions can be uploaded to reprogram the IMD. Typically, an IMD communicates with a programmer or a dedicated repeater located outside the body in a data exchange session. To minimize patient risk, wireless telemetry, such as inductive telemetry, is normally used to non-invasively communicate with the IMD.

Inductive telemetry has a few shortcomings. First, inductive telemetry is short range, typically about six centimeters, and requires close proximity between a patient and the programmer or repeater. The patient's movements are limited while data transfer is ongoing. Also, inductive telemetry typically has a slow data transfer rate, which is directly proportional to the carrier signal frequency. Only low frequency signals can be used for carrier signals due to the low-pass filtering effect of the metal casing of the IMD, resulting in a transmission speed of several kilobits per second. This transfer rate is inadequate for modern IMDs, which normally exchange thousands of kilobits of patient physiological data.

Recently, radio frequency (RF) telemetry has emerged as a viable adjunct to inductive telemetry, such as described in commonly-assigned U.S. Pat. No. 6,456,256, issued Sep. 24, 2002, to Amundson et al.; U.S. Pat. No. 6,574,510, to Von Arx et al., issued Jun. 3, 2003; and U.S. Pat. No. 6,614,406, issued Sep. 2, 2003, to Amundson et al., the disclosures of which are incorporated by reference. Unlike inductive telemetry, RF telemetry is long range, extending to 20 or more feet from a patient without using repeaters. This range allows a patient free movement while the IMD is accessed. RF telemetry also offers a higher data transfer rate that can significantly shorten download time.

Although promising, the use of RF telemetry in IMDs potentially raises serious privacy issues. Sensitive information, such as patient-identifiable health information, exchanged between an IMD and the programmer or repeater should be safeguarded to protect patient privacy. Prior to initiating a data exchange session, a clinician preferably first informs the patient and then proceeds only with the patient's knowledge. The short range of inductive telemetry can imply informed consent, but the longer range of RF telemetry can require additional precautions to safeguard any sensitive information against unauthorized disclosure or interception.

Recently enacted medical information privacy laws, including the Health Insurance Portability and Accountability Act (HIPAA) and the European Privacy Directive underscore the importance of safeguarding patients' privacy and require the protection of all patient-identifiable health information (PHI). Under HIPAA, PHI is defined as individually identifiable patient health information, including identifiable demographic and other information relating to the past, present or future physical or mental health or condition, or the provision or payment of health care to an individual that is created or received by a health care provider, health plan, employer or health care clearinghouse. Other types of sensitive information in addition to or in lieu of PHI could also be protectable.

The sweeping scope of medical information privacy laws, such as HIPAA, may affect patient privacy on IMDs with longer transmission ranges, such as provided through RF telemetry, and other unsecured data interfaces providing sensitive information exchange under conditions that could allow eavesdropping, interception or interference. Sensitive information should be encrypted prior to long range transmission. Currently available data encryption techniques, such as the Advanced Encryption Standard (AES), a FIPS-approved symmetric encryption algorithm, can satisfactorily safeguard sensitive information. These encryption techniques employ crypto keys, which are needed by both a sender and recipient to respectively encrypt and decrypt sensitive information transmitted during a data exchange session.

Encrypted data exchange sessions between an IMD and a programmer or repeater pose special concerns due to a potentially wide disparity in processing capabilities. Performing encryption, although computationally expensive in processing and storage resources, is well within the capabilities of a programmer or repeater. However, the same resource requirements can severely burden IMDs due to the modest, battery-powered processors typically used. The processing disparity can be in the order of four to five magnitudes. For instance, encrypting a 16 Kbyte message with the widely-used Z80 microprocessor running at processing speeds typical for an IMD, for instance, 1 MHz, can take up to 650 msec, which is unacceptably slow and costly in power and transmission bandwidth consumed. Moreover, the program code and data space for the encryption operations can strain limited on-board IMD memory space.

Therefore, there is a need for a system and method to safeguard sensitive information, particularly PHI, through preencryption when exchanged via long range telemetry or unsecured data interfaces. Preferably, such an approach would free the IMD from the burdens imposed by active encryption and decryption by preencrypting sensitive information stored but not used by the IMD with a programmer or repeater prior to transmission.

SUMMARY OF THE INVENTION

A crypto key is maintained on a secure key repository, such as on an IMD, and is used to preencrypt sensitive information, including any PHI, prior to storage on the IMD. The crypto key can either be pre-programmed and persistently stored on the IMD, or can be dynamically generated on the IMD, programmer or dedicated repeater. The crypto key is retrieved by the programmer or repeater from the source of the crypto key based on the form of the key and the type of device maintaining the crypto key, such as described in commonly-assigned U.S. patent application Ser. No. 10/800,806 entitled "System And Method For Securely Authenticating A Data Exchange Session With An Implantable Medical Device," filed Mar. 15, 2004, pending, the disclosure of which is incorporated by reference. The sensitive information is then encrypted by the programmer or repeater using the crypto key and is stored onto the IMD. Since the sensitive information is in an encrypted form, the encrypted sensitive information can be sent through secure, short range telemetry or using, for example, long range telemetry, such as RF telemetry, or other unsecured data interfaces. Subsequently, the encrypted sensitive information is retrieved from the IMD and is decrypted using the crypto key.

An embodiment provides a system and method for providing secure exchange of sensitive information with an implantable medical device. A crypto key uniquely associated with an implantable medical device is defined to encrypt sensitive information during a data exchange session. The crypto key is securely obtained over a secure connection from a secure key repository securely maintaining the crypto key. The sensitive information is encrypted using the crypto key and the sensitive information is stored as encrypted data onto the implantable medical device.

A further embodiment provides a system and method for securely maintaining sensitive information on an implantable medical device. Sensitive information encrypted using a crypto key uniquely associated with an implantable medical device is stored. Access is provided to the stored sensitive information exclusively over a secure connection Still other embodiments of the present invention will become readily apparent to those skilled in the art from the following detailed description, wherein are described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

DETAILED DESCRIPTION

Implantable Medical Device

Figure 1:
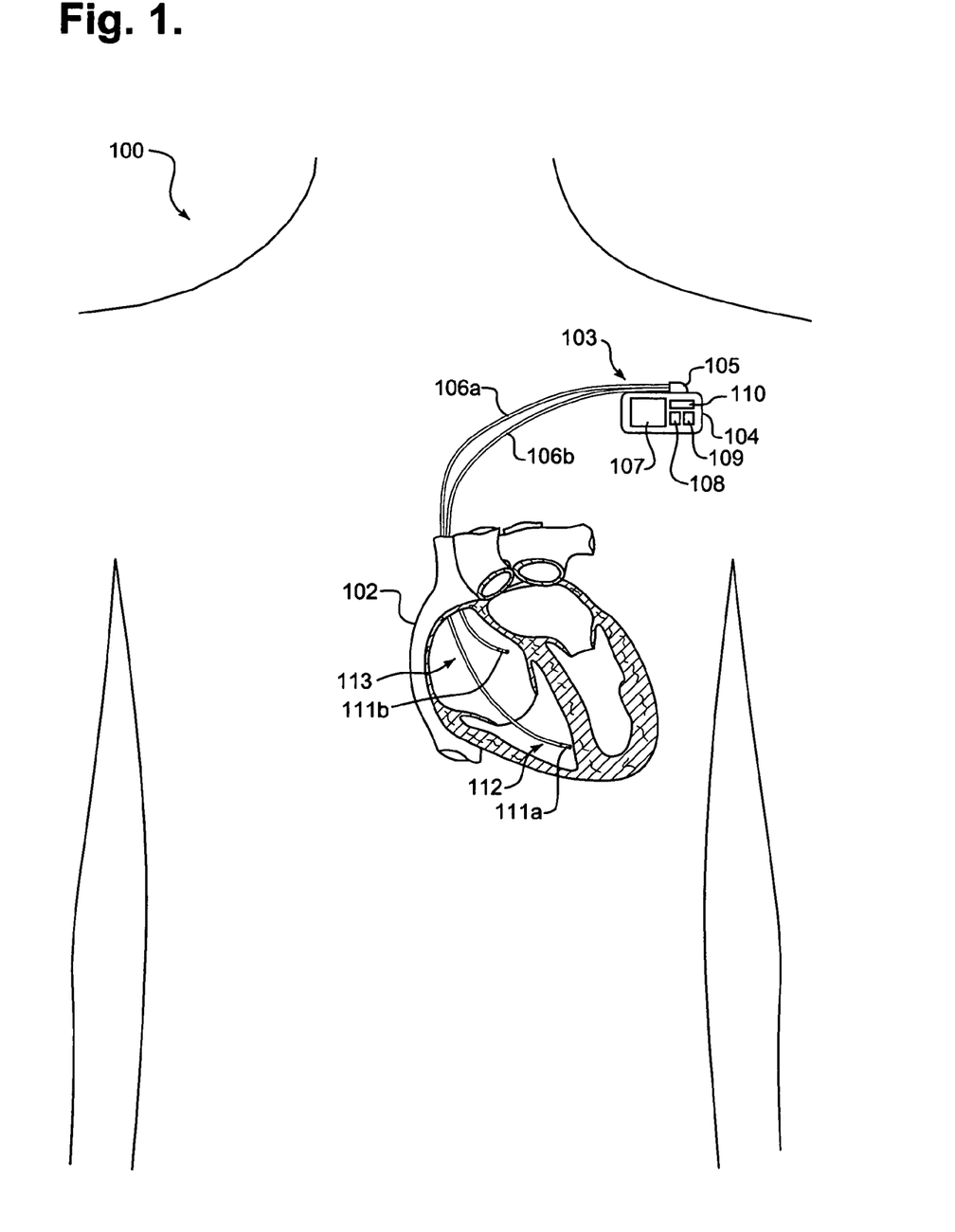
FIG. 1 is a block diagram showing, by way of example, an implantable medical device monitoring physiological parameters of a patient, in accordance with an embodiment of the present invention.

FIG. 1 is a block diagram 100 showing, by way of example, an implantable medical device (IMD) 103 monitoring physiological parameters of a patient, in accordance with an embodiment of the present invention. The IMD 103 is surgically implanted in the chest or abdomen of a patient and consists generally of a housing 104 and terminal block 105. The IMD 103 is coupled to a set of leads 106a-b at the terminal block 105. During surgery, the leads 106a-b are threaded through a vein and placed into the heart 102 with the distal tips of each lead 106a-b positioned in direct contact with tissue inside the heart 102.

The housing 104 contains a battery 107, control circuitry 108, memory 109, and telemetry circuitry 110. The battery 107 provides a finite power source for the IMD components. The control circuitry 108 samples and processes raw data signals and includes signal filters and amplifiers, memory and a microprocessor-based controller. The memory 109 includes a memory store in which static data can be stored for retrieval by health care providers and for use by the IMD 103. The memory 109 can also transiently store raw physiological signals for later retrieval and analysis. The telemetry circuitry 110 provides an interface between the IMD 103 and external devices, such as a programmer or dedicated repeater (not shown). The telemetry circuitry 110 enables operating parameters to be non-invasively programmed into the memory 109 through an external device in telemetric communication with the IMD 103. The telemetry circuitry 110 also allows static data to be received from and sent to the external device, as well as allowing patient information collected by the IMD 103 and transiently stored in the memory 109 to be sent to the external device.

The IMD 103 is in direct electrical communication with the heart 102 through electrodes 111a-b positioned on the distal tips of each lead 106a-b. By way of example, the set of leads 106a-b can include a right ventricular electrode 111a and a right atrial electrode 111b. The right ventricular electrode 111a is preferably placed in the right ventricular apex 112 of the heart 102 and the right atrial electrodes 111b is preferably placed in the right atrial chamber 113 of the heart 102. The electrodes 111a-b enable the IMD 103 to directly collect raw physiological measures, preferably through millivolt measurements. Other configurations and arrangements of leads and electrodes, including the use of single and multiple leads arrays and single and multiple electrodes, can be used, as would be recognized by one skilled in the art.

In the described embodiment, the IMD 103 can be implemented as part of cardiac pacemakers used for managing bradycardia, implantable cardioverter defibrillators (IMDs) used for treating tachycardia, and other types of implantable cardiovascular monitors and therapeutic devices used for monitoring and treating structural problems of the heart, such as congestive heart failure, as well as rhythm problems, as would be appreciated by one skilled in the art. Examples of cardiac pacemakers suitable for use in the described embodiment include the Pulsar Max II, Discovery, and Discovery II pacing systems, sold by Guidant Corporation, St. Paul, Minn. An example of an IMD suitable for use in the described embodiment includes the Contak Renewal cardiac resynchronization therapy defibrillator, also sold by Guidant Corporation, St. Paul, Minn.

On a regular basis, the raw physiological signals stored in the memory 109 are retrieved. By way of example, a programmer or repeater (not shown) can be used to retrieve the raw physiological signals. However, any form of programmer, repeater, interrogator, recorder, monitor, or transceiver suitable for communicating with IMD 103 could be used. In addition, a server, personal computer or digital data processor could be interfaced to the IMD 103, either directly or via a transceiver configured to communicate with the implantable medical device 103.

For short range data exchange, the IMD 103 communicates with the programmer or repeater through inductive telemetry signals exchanged through a wand placed over the location of the IMD 103. Programming or interrogating instructions and static data are sent to the IMD 103 and the stored raw physiological signals and the static data are downloaded into the programmer. For long range data exchange, the IMD 103 communicates with an external device capable of long range telemetry; such as a radio frequency (RF) programmer, repeater or other wireless computing device. Other types of data interfaces are possible, as would be appreciated by one skilled in the art. The static data can include protectable patient-identifiable health information (PHI), which is securely exchanged in encrypted form, as further described below with reference to FIG. 2.

In a further embodiment, the IMD 103 includes a telemetry interlock that limits communication between the IMD 103 and an external device. Patient/clinician authentication is secured through release of the telemetry interlock, which can be used in conjunction with secure crypto key 122 retrieval. The telemetry interlock is released when the external device transmits an ENABLE command to the IMD 103 via short range telemetry, such as described in commonly-assigned U.S. Pat. No. 7,155,290, issued Dec. 26, 2006, the disclosure of which is incorporated by reference.

In a further embodiment, the IMD 103 can verify the integrity of messages received from a programmer 123, repeater 124 or other wireless computing device 125 and, alternatively, a programmer 123, repeater 124 or other wireless computing device 125 can verify the integrity of messages received from IMD 103, both using a symmetric encryption algorithm or one-way hash algorithm, such as described in commonly-assigned U.S. Pat. No. 7,228,182, issued Jun. 5, 2007, the disclosure of which is incorporated by reference.

An example of a programmer with inductive telemetry is the Model 2920 Programmer Recorder Monitor, manufactured by Guidant Corporation, Indianapolis, Ind., which includes the capability to store retrieved static data and raw physiological signals on a removable floppy diskette. The static data and raw physiological signals could later be electronically transferred using a personal computer or similar processing device.

Other alternate static data and raw physiological signals transfer means could also be employed. For instance, the stored static data and raw physiological signals could be retrieved from the IMD 103 and electronically transferred to a network using a combination of a remote external programmer and analyzer and a remote telephonic communicator, such as described in U.S. Pat. No. 5,113,869, to Nappholz et al., issued May 19, 1992, the disclosure of which is incorporated by reference. Similarly, the stored static data and raw physiological signals could be retrieved and remotely downloaded to a server using a world-wide patient location and data telemetry system, such as described in U.S. Pat. No. 5,752,976, to Duffin et al., issued May 19, 1998, the disclosure of which is incorporated by reference.

Although described with reference to implantable cardiac monitoring and therapy delivery, IMDs also include neural stimulation, drug dispensing, and other implantable, as well as external, monitoring and therapy delivery devices, as would be appreciated by one skilled in the art.

Secure Exchange of Sensitive Information Process Flow

Figure 2:
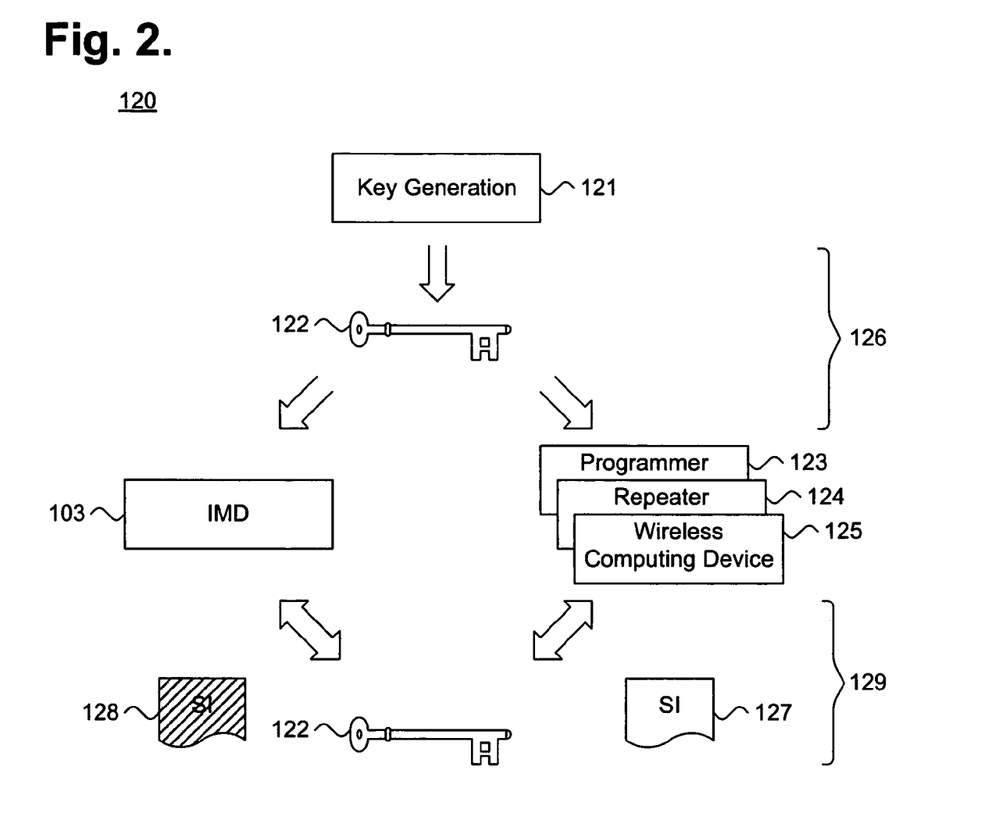
FIG. 2 is a process flow diagram showing a secure exchange of sensitive information.

FIG. 2 is a process flow diagram showing a secure exchange 120 of sensitive information. The secure exchange 120 includes key generation 121, authentication 126, and protected data storage and retrieval 129. Key generation 121 creates a crypto key 122, which is used to encrypt and decrypt any sensitive information exchanged with an IMD 103, such as during protected data storage and retrieval 129 using long range telemetry or over any other unsecured interface. The crypto key 122 can be statically generated and persistently stored, dynamically generated and persistently stored, dynamically generated and non-persistently stored as a session crypto key 122, or a combination of the foregoing. Persistently stored crypto keys 122 are maintained in a fixed secure key repository, such as a programmer, patient designator, secure database, token, or repeater, and on the IMD itself. Statically generated and persistently stored crypto keys are stored in the IMD 103 prior to implantation, such as during the manufacturing process. Dynamically generated and persistently stored crypto keys are generated dynamically, such as by a programmer 123 for subsequent download to the IMD 103 using short range telemetry following implantation. Dynamically generated and non-persistently stored session crypto keys are also generated dynamically and shared with the IMD 103, but are not persistently stored and are used for a single patient data exchange. Each crypto key 122 is uniquely assigned to the IMD 103. In one embodiment, the crypto key 103 has a length of 128 bits, is symmetric or is both 128-bits long and symmetric. Other crypto key lengths and symmetries are possible.

Authentication 126 involves an affirmative interaction between a patient and a clinician during which the clinician informs the patient, either directly or by implication, and secures authorization to access the patient information, including any static data constituting sensitive information, maintained in the IMD 103 and, if necessary, to interrogate and reprogram the IMD 103. Authentication 126 ensures that a clinician does not accidentally start a data exchange session with the wrong patient or without a patient's knowledge. Authentication 126 also provides an opportunity to securely obtain the crypto key 122 uniquely associated with the IMD 103. During authentication 126, the IMD 103 interfaces with an external source, such as a programmer 123, repeater 124 or other wireless computing device 125, to either receive or share the crypto key 122 assigned to the IMD 103, such as described in commonly-assigned U.S. patent application Ser. No. 10/800,806, entitled "System And Method For Securely Authenticating A Data Exchange Session With An Implantable Medical Device," filed Mar. 15, 2004, pending, the disclosure of which is incorporated by reference. In one embodiment, the external source retrieves the crypto key 122 from the IMD 103 using secure, short range telemetry, such as inductive telemetry, as further described below with reference to FIG. 4.

Authentication 126 must be completed prior to protected data storage and retrieval 129. Upon completing authentication 126, sensitive information 127 (SI), particularly PHI, is received into the external device from a patient or clinician and part or all of the sensitive information 127 is preencrypted by a programmer 123 or repeater 124 using the crypto key 122. Preencryption places the burden of active encryption and decryption on the external device, rather than on the IMD 103, for sensitive information stored but not actually used by the IMD 103. The preencrypted sensitive information 128 is then sent to the IMD 103. The preencrypted sensitive information 128 can be sent through secure, short range telemetry or using, for example, long range telemetry, such as RF telemetry, or other unsecured data interfaces. Preencryption allows sensitive information to be securely transmitted over an RF or other long range wireless link in compliance with applicable patient health information privacy laws and regulations. If the sensitive information needs to be retrieved, the external source obtains the crypto key 122, if necessary, through authentication 126 and retrieves the encrypted information 128 from the IMD 103 for subsequent decryption using the crypto key 122. In one embodiment, the sensitive information 127, including any PHI, is encrypted using a standard encryption protocol, such as the Advanced Encryption Standard protocol (AES). Other authentication and encryption techniques and protocols, as well as other functions relating to the use of the crypto key 122 are possible, including the authentication and encryption techniques and protocols described in commonly-assigned U.S. Pat. No. 7,155,290, issued Dec. 26, 2006, the disclosure of which is incorporated by reference.

Preencryption unburdens the IMD 103 by not requiring the IMD 103 to encrypt or decrypt sensitive information that is not actually needed by the IMD 103. However, in a further embodiment, the sensitive information 103 may also be needed by the IMD 103, for example, to properly configure operational parameters based on the physical characteristics of the patient, such as height and weight measurements. Accordingly, a copy of part or all of the sensitive information 127 is stored on the IMD 103 in unencrypted form by sending the sensitive information 127 through secure, short range telemetry. The unencrypted sensitive information 127 can thereafter be retrieved only through secure, short range telemetry to ensure proper safeguarding. Both encrypted and unencrypted sensitive information can be simultaneously stored on the IMD 103.

Patient Health Information Record

Figure 3:
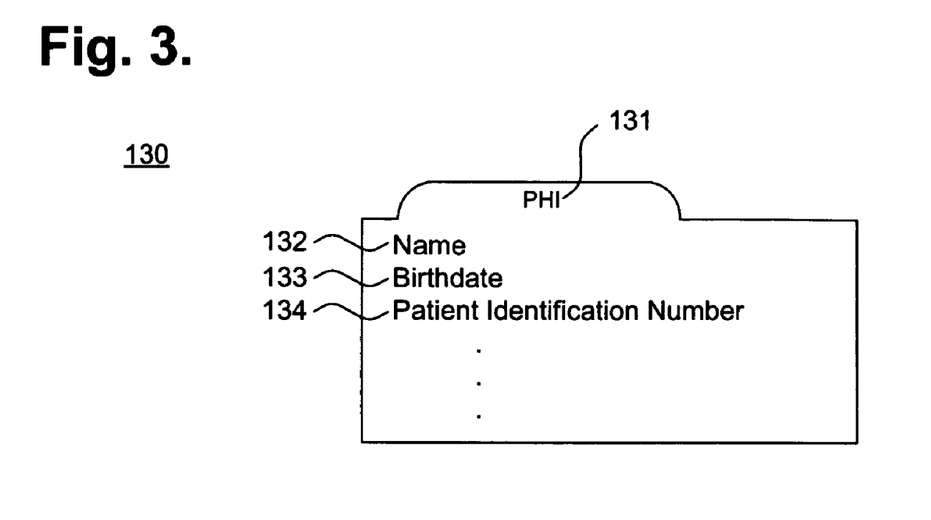
FIG. 3 is a data structure diagram showing a patient health information record.

FIG. 3 is a data structure diagram 130 showing a patient health information (PHI) record 131. At a minimum, patient health information is sensitive information 127 that identifies a particular individual to health- and medical-related information. Under HIPAA, there are eighteen categories of patient health information that require protection and include, for example, name 132, birthdate 133, and patient identification number 134. Protectable patient health information can include one or more of the eighteen categories, which can be stored in encrypted form. In addition, each record 131 can also include other types of identifying and treatment profile information, medical history, and other pertinent data. Other types of sensitive information in addition to or in lieu of PHI could also be protectable.

System for Providing Secure Exchange of Sensitive Information

Figure 4:
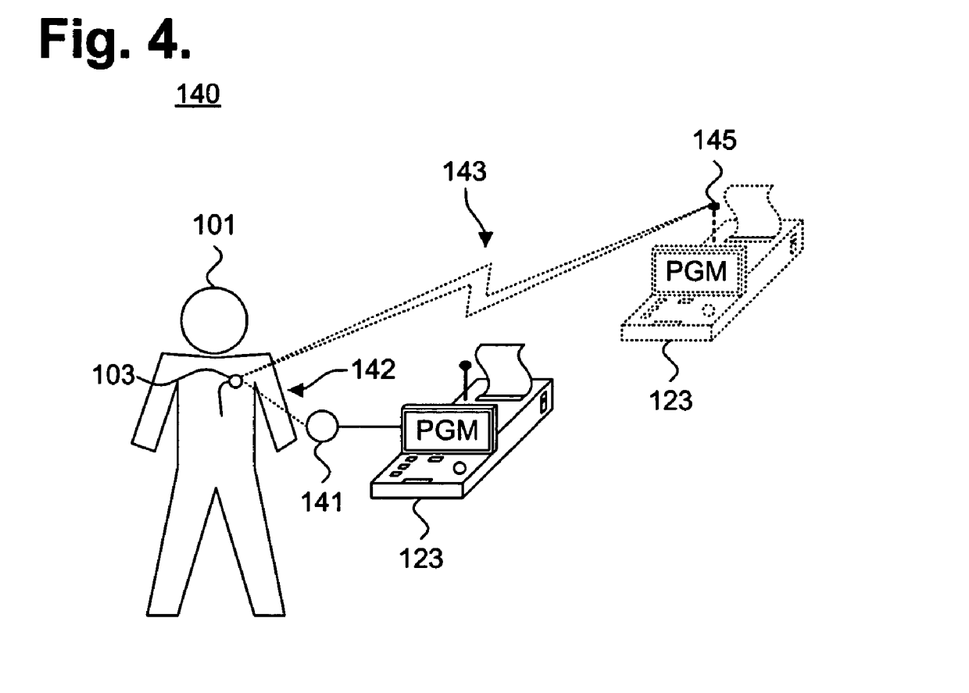
FIG. 4 is a functional block diagram showing, by way of example, a system for providing secure exchange of sensitive information with an implantable medical device, in accordance with an embodiment of the present invention.

FIG. 4 is a functional block diagram showing, by way of example, a system 140 for providing secure exchange of sensitive information with an implantable medical device 103, in accordance with an embodiment of the present invention. The crypto key 122 is either preprogrammed and persistently stored in the IMD 103 prior to implantation, such as during the manufacturing process, or is generated dynamically by the IMD 103 or by a programmer 123 for subsequent download to the IMD 103 using short range telemetry following implantation. The crypto key 122 is preferably a 128-bit key and can be symmetric or asymmetric.

The IMD 103 includes an on-board RF transceiver (not shown), which interfaces through long range telemetry with a remote RF transceiver. The on-board transceiver is integrated into the IMD 103 with a circumferential antenna wrapping around the external casing of the IMD 103, such as described in commonly-assigned U.S. Pat. No. 6,456,256, to Amundson, issued Sep. 24, 2002, the disclosure which is incorporated by reference. RF communication is performed either by varying the frequency, phase angle or amplitude of the electromagnetic energy radiated by the on-board RF transceiver, such as described in commonly-assigned U.S. Pat. No. 6,574,510, to Von Arx et al., issued Jun. 3, 2003, the disclosure which is incorporated by reference.

In one embodiment, the crypto key 122 is stored in the IMD 103 prior to implantation and patient/clinician authentication 126 is provided through a short range telemetric link 142 between the programmer 123 and IMD 103 using inductive telemetry. A wand 141 is placed over the location of the IMD 103, which sends the crypto key 122 to the programmer 123 over the telemetric link 142. The personal interaction between the patient and clinician ensures that patient/clinician authentication 126 is completed.

Upon receiving the crypto key 122, the programmer 123 uses the crypto key 122 to encrypt sensitive information 127, including any PHI. The sensitive information is then sent to the IMD 103 as encrypted sensitive information 128 for subsequent retrieval by health care providers. The encrypted sensitive information 128 is sent to the IMD 103 either over a short range telemetric link 142 or over a long range telemetric link 143 using RF telemetry. The IMD 103 interfaces to an RF transceiver 145 integral to the programmer 123. Similarly, the programmer 123 retrieves the encrypted sensitive information 128 from the IM 103 and uses the crypto key 122 to decrypt the encrypted sensitive information 128 back into unencrypted sensitive information 127. In a further embodiment, an unencrypted copy of part or all of the sensitive information 127 is stored onto the IMD 103 by the programmer 123 over a short range telemetric link 142. To ensure patient privacy, the unencrypted sensitive information 127 is only retrieved from the IMD 103 over a short range telemetric link 142.

The IMD 103 communicates with the programmer 123 via the wand 141 through short range telemetry. Short range telemetry includes, nonexclusively, inductive telemetry. Data is digitally exchanged between the IMD 103 and the programmer 123 using standard protocols, such as ASK (amplitude shift key), FSK (frequency shift key), PSK (phase shift key) and QPSK (quadrature phase shift key). Signals are inductively exchanged through the wand 141, such as described in commonly-assigned U.S. Pat. No. 4,562,841, to Brockway et al., issued Jan. 2, 1986, the disclosure which is incorporated by reference.

In a further embodiment, one or more repeaters (not shown) augment the long range telemetric communication by relaying the telemetric signals from the on-board RF transceiver of the IMD 103 to a secure server, which can provide secure on-line data access over a network, such as the Internet, to authorized health care providers and medical professional.

Secured Area Definition

Figure 5:
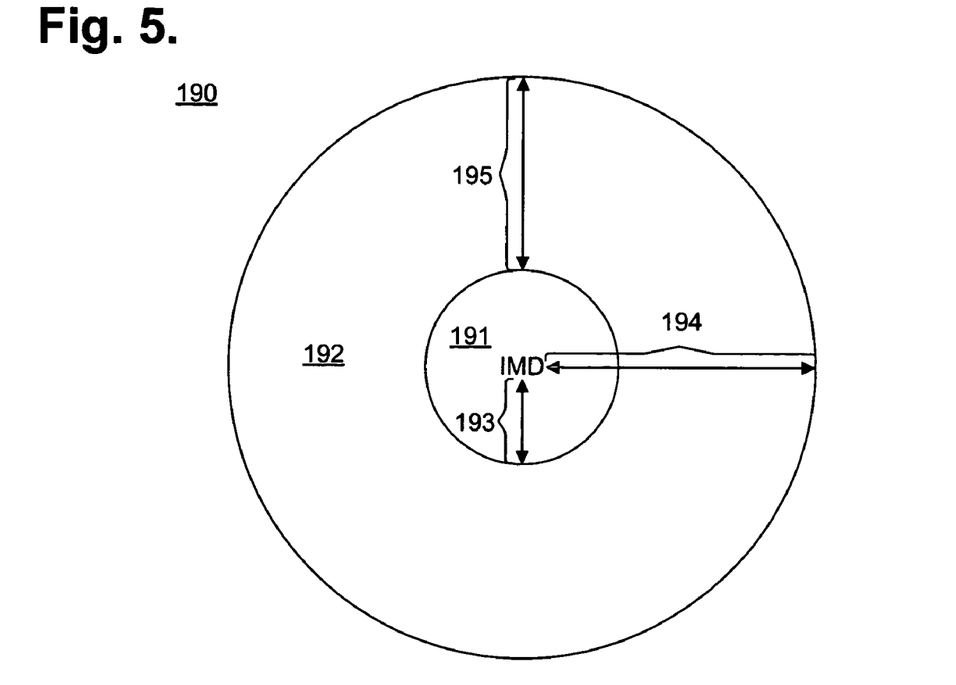
FIG. 5 is a block diagram showing, by way of example, a secure area defined around an IMD.

FIG. 5 is a block diagram 190 showing, by way of example, a secured area defined around an IMD 103. Patient/clinician authentication 126 can only be transacted within a logically defined secured area 191, whereas data exchange session can be transacted in a logically defined non-secured area 192, provided patient/clinician authentication 126 is successfully completed and all patient information exchanged is properly encrypted.

The range 193 of the secured area 191 is based on the form of patient/clinician authentication 126 transacted. For example, short range inductive telemetry has a range 193 of about six centimeters. The range of the non-secured area 194 similarly depends on the form of long range telemetry used. For RF telemetry, the range 194 can be 20 or more feet from the patient, depending on patient orientation relative to the programmer 123 or repeater 124. The use of encryption enables the range 193 of the secured area 191 to have an extended range 195 provided by the non-secured area 192 through encryption or authentication.

Method Overview

Figure 6:
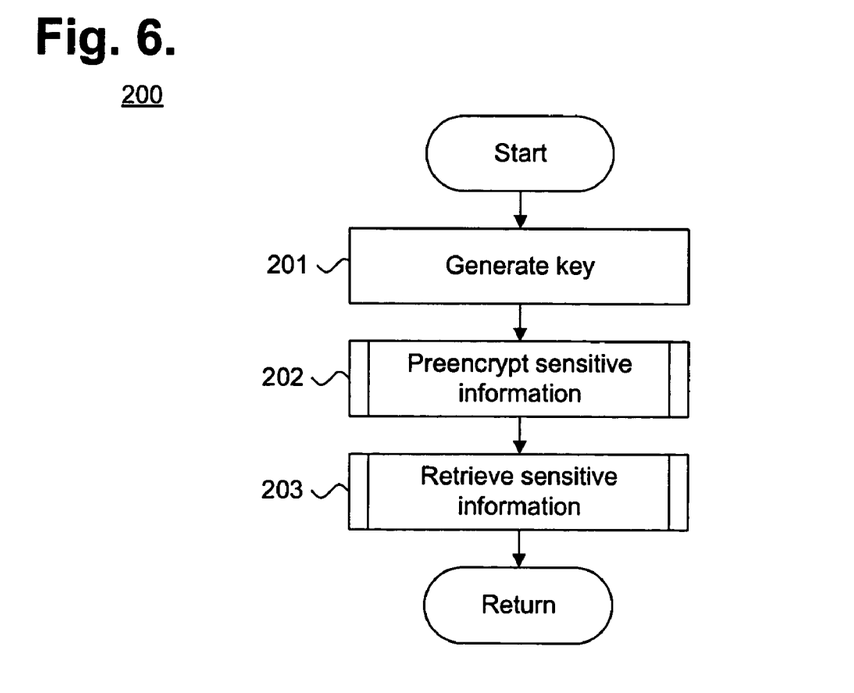
FIG. 6 is a flow diagram showing a method for providing secure exchange of sensitive information with an implantable medical device, in accordance with embodiments of the present invention.

FIG. 6 is a flow diagram showing a method 200 for providing secure exchange of sensitive information 127 with an implantable medical device 103, in accordance with an embodiment of the present invention. The method 200 is described as a sequence of process operations or steps, which can be executed, for instance, by the programmer 123, repeater 124, or other components.

Initially, the crypto key 122 is generated (block 201). Depending upon the system, the crypto key 122 could be generated dynamically by a programmer 123 or, if applicable, the repeater 124, for subsequent download to the IMD 103 using short range telemetry following implantation. Similarly, the crypto key 122 could be generated during the manufacturing process and persistently stored in the IMD 103 prior to implantation. Alternatively, the crypto key 122 could be dynamically generated by the IMD 103. The sensitive information 127 is preencrypted using the crypto key 122 and stored onto the IMD 103 as encrypted sensitive information 128 (block 202), as further described below with reference to FIG. 7. Subsequently, the encrypted sensitive information 128 is retrieved from the IMD 103 and decrypted back into sensitive information 127 using the crypto key 122 (block 203), as further described below with reference to FIG. 7. The method then terminates.

Sensitive Information Preencryption

Figure 7:
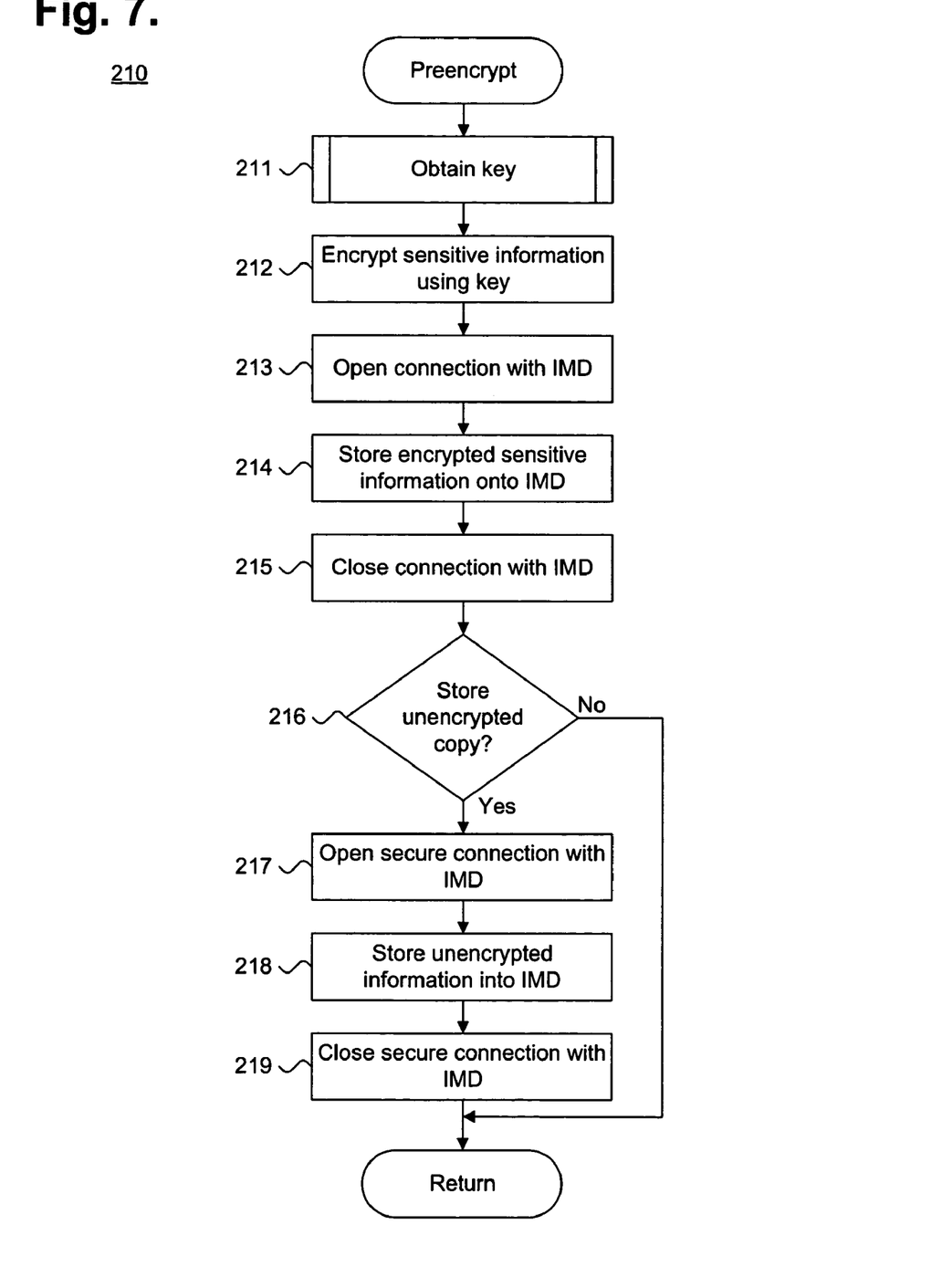
FIG. 7 is a flow diagram showing a routine for preencrypting sensitive information for use in the method of FIG. 6.

FIG. 7 is a flow diagram showing a routine 210 for preencrypting sensitive information 127 for use in the method 200 of FIG. 6. The purpose of this routine is to encrypt sensitive information 127, including any PHI, using a crypto key 122 retrieved through secure means, and to store the encrypted sensitive information 128 onto an IMD 103.

Initially, the crypto key 122 is obtained via a secure connection to a secure key repository (block 211), as further described below with reference to FIG. 9. Upon successfully obtaining the crypto key 122, sensitive information 127, including any PHI, is encrypted using the crypto key 122 (block 212). A connection is established between the IMD 103 and the programmer 123 (block 213). The connection can be either a short range telemetric link 142 or a long range telemetric link 143. The encrypted sensitive information 128 is then stored onto the IMD 103 (block 214) and the connection between the IMD 103 and the programmer 123 is closed (block 215).

In a further embodiment, part or all of the sensitive information 127 is stored on the IMD 103 in unencrypted form. If unencrypted sensitive information 127 is being stored (block 216), a secure connection is established between the IMD 103 and the programmer 123 (block 217). The secure connection must use a short range telemetric link 142 to ensure patient privacy. The unencrypted sensitive information 127 is then stored onto the IMD 103 (block 218) and the secure connection between the IMD 103 and the programmer 123 is closed (block 219). The routine then returns.

Encrypted Sensitive Information Retrieval

Figure 8:
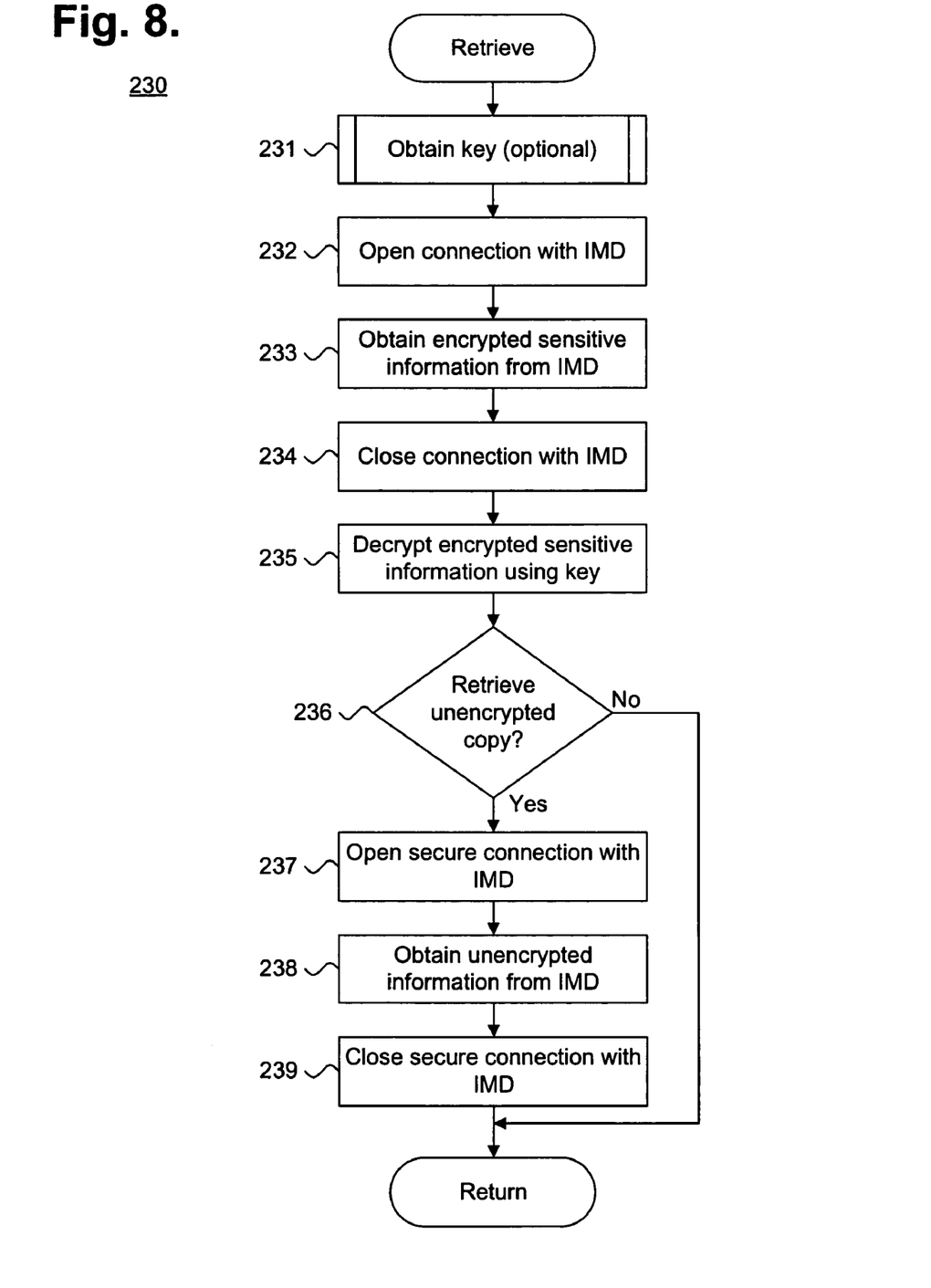
FIG. 8 is a flow diagram showing a routine for retrieving encrypted sensitive information for use in the method of FIG. 6.

FIG. 8 is a flow diagram showing a routine 230 for retrieving encrypted sensitive information 128 for use in the method 200 of FIG. 6. The purpose of this routine is to retrieve encrypted sensitive information 128, including any PHI, from an IMD 103 and to decrypt the encrypted sensitive information 128 using a crypto key 122.

Initially, the crypto key 122 is optionally obtained via a secure connection to a secure key repository (block 231), as further described below with reference to FIG. 9. The crypto key 122 only need be obtained if the programmer 123 requires a copy of the crypto key 122. A connection is established between the IMD 103 and the programmer 123 (block 232). The connection can be either a short range telemetric link 142 or a long range telemetric link 143. Encrypted sensitive information 127, including any PHI, is retrieved from the IMD 103 (block 233) and the connection between the IMD 103 and the programmer 123 is closed (block 234). The encrypted sensitive information 128 is then decrypted using the crypto key 122 (block 235).

In a further embodiment, part or all of the sensitive information 127 is stored on the IMD 103 in unencrypted form. If unencrypted sensitive information 127 is being retrieved (block 236), a secure connection is established between the IMD 103 and the programmer 123 (block 237). The secure connection must use a short range telemetric link 142 to ensure patient privacy. The unencrypted sensitive information 127 is then retrieved from the IMD 103 (block 238) and the secure connection between the IMD 103 and the programmer 123 is closed (block 239). The routine then returns.

Obtaining a Crypto Key

Figure 9:
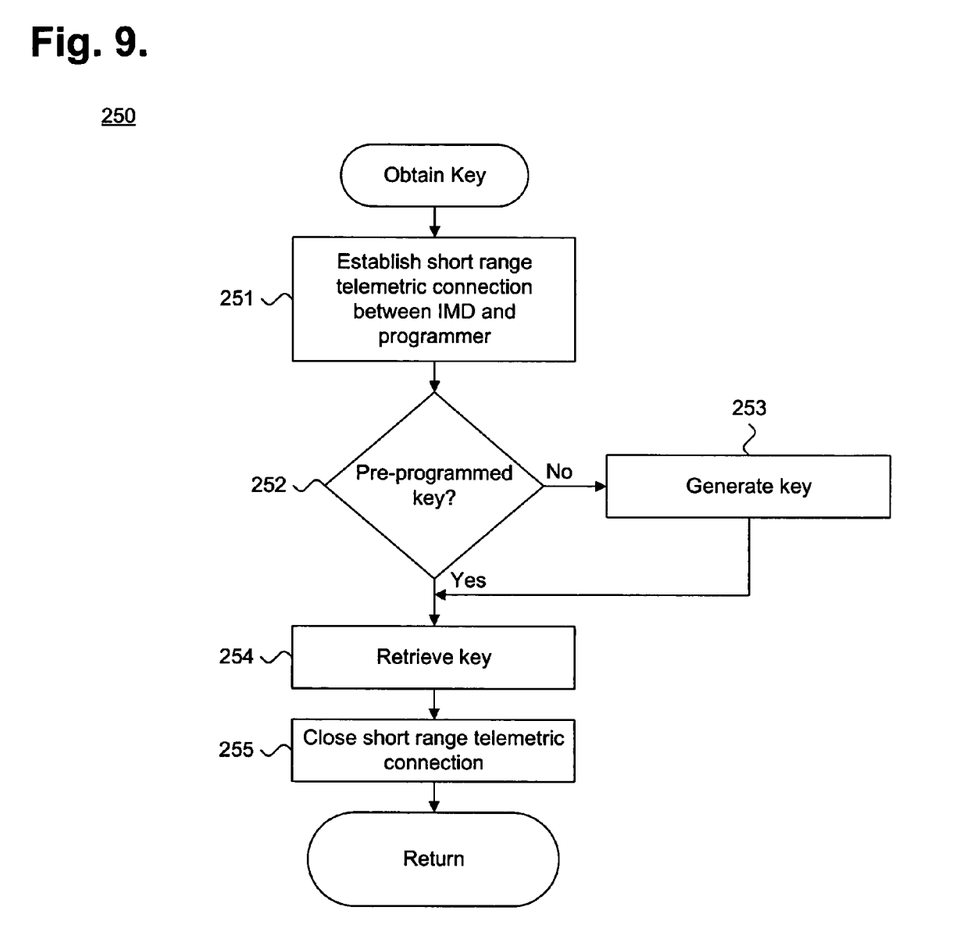
FIG. 9 is a flow diagram showing a routine for obtaining a crypto key for use in the methods of FIGS. 7 and 8.

FIG. 9 is a flow diagram showing a routine 250 for obtaining a crypto key 122 for use in the methods 210, 230 of FIGS. 7 and 8. One purpose of this routine is to retrieve a crypto key 122 matching a crypto key 122 pre-programmed and persistently stored in an IMD 103.

A short range telemetry connection is established between the IMD 103 and the programmer 123 (block 251). If the crypto key 122 is pre-programmed, that is, persistently stored on the IMD 103 (block 252), the crypto key 122 is retrieved from the IMD 103 (block 254) over the short range telemetric link. Otherwise, if the crypto key 122 is not pre-programmed (block 252), the IMD 103 generates the crypto key 122 (block 253), which is then retrieved by the programmer 123 (block 254). In a further embodiment, the programmer 123 dynamically generates the crypto key 122, which is downloaded to the IMD 103. Upon the successful retrieval of the crypto key from IMD 103, the short range telemetric connection is closed (block 255). The routine then returns.

In further embodiment, the crypto key 122 is retrieved using a patient designator, through a secure lookup, using a physical token, and with a repeater to provide patent/clinician authentication, such as described in commonly-assigned U.S. patent application Ser. No. 10/800,806; entitled "System And Method For Securely Authenticating A Data Exchange Session With An Implantable Medical Device," filed Mar. 15, 2004, pending, the disclosure of which is incorporated by reference.

While the invention has been particularly shown and described as referenced to the embodiments thereof, those skilled in the art will understand that the foregoing and other changes in form and detail may be made therein without departing from the spirit and scope of the invention.

What is claimed is:

1. A system for providing secure exchange of sensitive information with an implantable medical device, comprising:
   a crypto key uniquely associated with an implantable medical device to encrypt sensitive information during a data exchange session; and
   an external source, comprising:
      a key module configured to securely obtain the crypto key over a secure connection from a secure key repository securely maintaining the crypto key and further configured to encrypt the sensitive information using the crypto key;
      a long range transmission module configured to transmit the encrypted sensitive information to the implantable medical device via a long range interface and further configured to store the encrypted sensitive information onto the implantable medical device; and
      a short range transmission module configured to further transmit a copy of at least a part of the sensitive information to the implantable medical device via a secure short range interface and further configured to store the copy as unencrypted data onto the implantable medical device.

2. A system according to claim 1, wherein the short range interface logically defines a secured area around the implantable medical device within which to securely obtain the crypto and the long range interface logically defines a non-secured area extending beyond the secured area within which to exchange the encrypted sensitive information.

3. A system according to claim 1, wherein the encrypted sensitive information is retrieved from the implantable medical device over a non-secure connection and the encrypted sensitive information is decrypted using the crypto key.

4. A system according to claim 3, wherein the crypto key is securely retrieved over a secure connection from the secure key repository prior to decrypting the encrypted sensitive information.

5. A system according to claim 3, wherein the encrypted sensitive information is retrieved through long range telemetry.

6. A system according to claim 5, wherein the long range telemetry comprises radio frequency telemetry.

7. A system according to claim 1, wherein the unencrypted data is securely retrieved from the implantable medical device over a secure connection.

8. A system according to claim 1, wherein the crypto key is securely retrieved from the secure key repository through a programmer.

9. A system according to claim 1, wherein the crypto key is maintained on the implantable medical device, and the crypto key is retrieved through short range telemetry.

10. A system according to claim 9, wherein the short range telemetry comprises inductive telemetry.

11. A system according to claim 1, wherein the external source comprises at least one of a programmer and a repeater.

12. A system according to claim 1, wherein the crypto key comprises an encryption key in accordance with the Advanced Encryption Standard.

13. A method for providing secure exchange of sensitive information with an implantable medical device, comprising:
    defining a crypto key uniquely associated with an implantable medical device to encrypt sensitive information during a data exchange session;
    securely obtaining the crypto key over a secure connection from a secure key repository securely maintaining the crypto key;
    encrypting the sensitive information using the crypto key, transmitting the encrypted sensitive information to the implantable medical device via a long range interface, and storing the encrypted sensitive information onto the implantable medical device; and
    further transmitting a copy of at least a part of the sensitive information to the implantable medical device via a secure short range interface and storing the copy as unencrypted data onto the implantable medical device.

14. A method according to claim 13, further comprising:
    logically defining a secured area around the implantable medical device within which to securely obtain the crypto key; and
    logically defining a non-secured area extending beyond the secured area within which to exchange the encrypted sensitive information.

15. A method according to claim 13, further comprising:
    retrieving the encrypted sensitive information from the implantable medical device over a non-secure connection; and
    decrypting the encrypted sensitive information using the crypto key.

16. A method according to claim 15, further comprising:
    securely retrieving the crypto key over a secure connection from the secure key repository prior to decrypting the encrypted sensitive information.

17. A method according to claim 15, further comprising:
    retrieving the encrypted sensitive information through long range telemetry.

18. A method according to claim 17, wherein the long range telemetry comprises radio frequency telemetry.

19. A method according to claim 13, further comprising:
    securely retrieving the unencrypted data from the implantable medical device over a secure connection.

20. A method according to claim 13, wherein the crypto key is securely retrieved from the secure key repository through a programmer.

21. A method according to claim 13, further comprising:
    maintaining the crypto key on the implantable medical device; and
    retrieving the crypto key through short range telemetry.

22. A method according to claim 21, wherein the short range telemetry comprises inductive telemetry.

23. A method according to claim 13, wherein the external source comprises at least one of a programmer and a repeater.

24. A method according to claim 13, wherein the crypto key comprises an encryption key in accordance with the Advanced Encryption Standard.

25. An apparatus for securely transacting a data exchange session with an implantable medical device, comprising:
    means for defining a crypto key uniquely associated with an implantable medical device to encrypt sensitive information during a data exchange session;
    means for securely obtaining the crypto key over a secure connection from a secure key repository securely maintaining the crypto key;
    means for encrypting the sensitive information using the crypto key, means for transmitting the encrypted sensitive information to the implantable medical device via a long range interface, and means for storing the encrypted sensitive information onto the implantable medical device; and
    means for further transmitting a copy of at least a part of the sensitive information to the implantable medical device via a secure short range interface and means for storing the copy as unencrypted data onto the implantable medical device.

26. An implantable medical device for securely maintaining sensitive information, comprising:
- a receiver to receive sensitive information via a long range interface and a copy of at least a part of the sensitive information via a short range interface;
- a memory to store the sensitive information encrypted using a crypto key uniquely associated and to further store the copy as unencrypted data; and
- a secure interface to provide access to the stored sensitive information exclusively over a secure connection.

27. An method for securely maintaining sensitive information on an implantable medical device, comprising:
- receiving sensitive information via a long range interface and a copy of at least a part of the sensitive information via a short range interface;
- storing the sensitive information encrypted using a crypto key uniquely associated with an implantable medical device and further storing the copy as unencrypted data; and
- providing access to the stored sensitive information exclusively over a secure connection.

28. An apparatus for securely maintaining sensitive information on an implantable medical device, comprising:
- means for receiving sensitive information via a long range interface and a copy of at least a part of the sensitive information via a short range interface;
- means for storing the sensitive information encrypted using a crypto key uniquely associated with an implantable medical device and the copy as unencrypted data; and means for providing access to the stored sensitive information exclusively over a secure connection.

* * * * *